United States Patent [19]

Acher et al.

[11] Patent Number: 4,804,765

[45] Date of Patent: Feb. 14, 1989

[54] PROCESS FOR SYNTHESIZING N-[(1'-ALLYL-2'PYRROLIDINYL) METHYL]2-METHOXY-4,5-AZIMIDOBENZAMIDE

[75] Inventors: Jacques Acher, Itteville; Jean-Claude Monier, Lardy, both of France

[73] Assignee: Societe D'Etudes Scientifiques et Industrielles de L'Ile-d-France, Paris, France

[21] Appl. No.: 810,669

[22] Filed: Dec. 18, 1985

[30] Foreign Application Priority Data

Dec. 18, 1984 [FR] France ................................ 84 19322

[51] Int. Cl.$^4$ ...................... A61K 31/41; C07D 249/18
[52] U.S. Cl. ...................... 548/259; 548/261; 548/567; 562/437; 562/458; 564/183
[58] Field of Search ................. 548/579, 259, 260, 261

[56] References Cited

U.S. PATENT DOCUMENTS

| | | | |
|---|---|---|---|
| 3,839,330 | 10/1974 | Thominet | 514/872 |
| 4,039,672 | 8/1977 | Bulteau | 548/259 |
| 4,146,630 | 3/1979 | Kampe | 514/332 |
| 4,294,828 | 10/1981 | Thominet | 548/566 |
| 4,673,686 | 6/1987 | Thominet | 548/259 |

FOREIGN PATENT DOCUMENTS 517588 10/1955 Canada .............................. 548/579
1795110 1/1973 Fed. Rep. of Germany ...... 548/259

OTHER PUBLICATIONS

Albertson, from *Organic Reactions*, v. 12 (John Wiley and Sons, N.Y.) 1962, pp. 162–165 and 189–196.
Carey and Sundberg, *Advanced Organic Chemistry*, Part B (1977) (Plenum Press, N.Y.), p. 476.
March, *Advanced Organic Chemistry*, 2nd ed. (1977) (McGraw Hill Book Co. N.Y.) p. 383.
Balcom, D., J. Am. Chem. Soc. (1953), v. 75, 4334.
Pollack, R. M., J. Am. Chem. Soc. (1970) v. 92, 7190–7194.

*Primary Examiner*—Donald G. Daus
*Assistant Examiner*—Mark W. Noel
*Attorney, Agent, or Firm*—Fitzpatrick, Cella, Harper & Scinto

[57] ABSTRACT

The invention concerns a novel process for the synthesis of N-[(1'-allyl-2'-pyrrolidinyl) methyl]-2-methoxy-4,5-azimidobenzamide, which successively comprises the preparation of 2-methoxy-4,5-diaminobenzoic acid, 2-methoxy-4,5-diacetylaminobenzoic acid, N-(2',5'-dihalopentyl)-2-methoxy-4,5-diacetylaminobenzamide, N-[(1'-allyl-2'-pyrrolidinyl) methyl]-2-methoxy-4,5-diacetylaminobenzamide and then N-[(1'-allyl-2'-pyrrolidinyl) methyl]-2-methoxy-4,5-azimido benzamide.

1 Claim, No Drawings

PROCESS FOR SYNTHESIZING N-[(1'-ALLYL-2'PYRROLIDINYL) METHYL]2-METHOXY-4,5-AZIMIDOBENZAMIDE

BACKGROUND OF THE INVENTION

The invention concerns a novel process for the synthesis of N-[(1'-allyl-2'-pyrrolidinyl) methyl]2-methoxy-4,5-azimidobenzamide of the following formula:

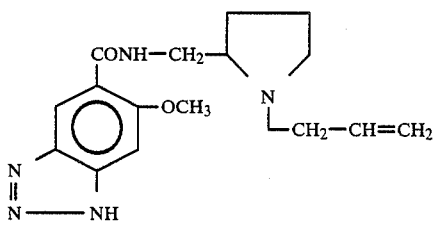

That compound and its preparation are described in U.S. Pat. No. 4,039,672, issued Aug. 2, 1977. The compound is useful as a medicament and in particular, has therapeutic benefits in the gastro-enterological field.

The presence of an amide function in the molecule has permitted a conventional synthesis by the condensation of 2-methoxy-4,5-azimidobenzoic acid and N-allyl-2-aminomethyl pyrrolidine, as precursors, either directly or by way of a reactive derivative of 2-methoxy-4,5-azimidobenzoic acid or N-allyl-2-aminomethyl pyrrolidine. For example, 2-methoxy-4,5-azimidobenzoic acid has been reacted with products obtained (1) by the preliminary reaction of the precursor amine with phosphorus chlorides, phosphorus oxychloride or substituted chlorophosphites, or (2) by the preliminary reaction of an isocyanate with the precursor amine Further, esters (alkyl or cyanomethyl or methoxymethyl esters) or amides, azides, mixed or symmetrical acid anhydrides, and other derivatives of 2-methoxy 4,5-azimidobenzoic acid can be reacted with N-allyl 2-aminomethyl pyrrolidine to form the Title compound Such conventional processes all require the use of starting materials which are not generally commercially available. The difficulty in obtaining such reactants is a drawback to the synthesis of the Title compound.

SUMMARY OF THE INVENTION

The present invention includes a process for synthesizing N-[(1'-allyl-2'-pyrrolidinyl)methyl]-2-methoxy-4,5-azimido benzamide comprising, in sequence the steps of:

(a) reacting methyl-2-methoxy-4-acetylamino-5-nitrobenzoate with sodium hydroxide to form sodium 2-methoxy-4-amino-5-nitrobenzoate;

(b) reacting the sodium 2-methoxy-4-amino-5-nitrobenzoate with hydrazine in the presence of Raney nickel to form 2-methoxy-4,5-diaminobenzoic acid;

(c) reacting the 2-methoxy-4,5-diaminobenzoic acid with acetic anhydride to form 2-methoxy-4,5-diacetylaminobenzoic acid;

(d) reacting the 2-methoxy-4,5-diacetylaminobenzoic acid with a lower alkyl chloroformate to form a mixed lower alkanoic-benzoic anhydride of said 2-methoxy-4,5-diacetylamino benzoic acid.

(e) reacting the mixed anhydride with a dihalopentylamine to form N-(2',5'-dihalopentyl)-2-methoxy-4,5-diacetylamino benzamide;

(f) reacting the N-(2',5'-dihalopentyl)- 2-methoxy-4,5-diacetylaminobenzamide with allylamine to form N-[(1'-allyl-2'-pyrrolidinyl) methyl]-2-methoxy-4,5-diacetylaminobenzamide; and (g) reacting the N-[(1'-allyl-2'-pyrrolidinyl) methyl]-2-methoxy-4,5-diacetylaminobenzamide with sodium nitrite.

Novel synthesis intermediates of the invention include 2-methoxy-4,5-diacetylamino benzoic acid; N-(2',5'-dihalopentyl)-2-methoxy-4,5-diacetylminobenzamide and N-[(1'-allyl-2'-pyrrolidinyl) methyl]2-methoxy-4,5-diacetylaminobenzamide.

The synthesis of the invention can be applied on an industrial scale, to provide for suitable production of N-[(1'-allyl-2'-pyrrolindinyl) methyl]-2-methoxy-4,5-azimidobenzamide.

In prior art syntheses, as illustrated in U.S. Pat. No. 4,039,672, involving preparation of 2-methoxy-4,5-azimidobenzoic acid, as a reactant, it is necessary to use an autoclave in order to reduce the 5-nitro intermediate to the 5-amino intermediate. The present method eliminates that disadvantage, and does not require that the steps of the process to be carried out under pressure. It is therefore possible to manufacture large amounts of product in a single operation, which is an important industrial advantage, since the size of a specific reactor no longer constitutes a limitation.

DETAIL DESCRIPTION OF THE INVENTION

The starting compound in the synthesis, methyl-2-methoxy-4-acetylamino-5-nitrobenzoate, is known to the art.

In general, reaction of methyl 2-methoxy-4-acetylamino-5-nitrobenzoate with the base is preferably immediately followed by the in-situ reaction of the intermediate sodium-2-methoxy- 4-amino-5-nitrobenzoate (intermediate I) with hydrazine or its equivalent, preferably as hydrazine hydrate, to form 2-methoxy-4,5-diaminobenzoic acid (intermediate II). That product is preferably recovered and purified prior to further use.

Intermediate II is reacted with acetic anhydride or its equivalent and the resulting product, 2-methoxy-4,5-diacetylaminobenzoic acid, (intermediate III) is preferably recovered and purified.

Intermediate III is then solubilized in the presence of a base, such as triethylamine, and agitated until it is dissolved. The reaction mix is cooled and a lower alkyl chloroformate is slowly added. The lower alkyl chloroformate is preferably a $C_1$ to $C_5$ alkyl chloroformate. Preferred alkyl chloroformates include isobutyl chloroformate and, most preferably, ethyl chloroformate. A mixed anhydride (intermediate IV) is formed in-situ. It is then preferable to add the 2,5-dihalopentylamine, as a hydrochloride or its equivalent, to the reaction mix to form an N-(2',5'-dihalopentyl)-2-methoxy-4,5-diacetylaminobenzamide (intermediate V). The 2',5'-dihalopentylamine employed is preferably 2',5'-dibromopentylamine, and, most preferably, 2'-5'-dichloropentylamine. Intermediate V, a novel compound, is preferably recovered and purified prior to further use.

Thereafter, intermediate V is reacted with allylamine or its equivalent and the resulting product, N-[(1'-allyl-2'-pyrrolidinyl)methyl]-2-methoxy-4,5-diacetylaminobenzamide, intermediate VI, a novel compound, is preferably recovered and purified prior to further use.

Finally, intermediate VI is reacted with sodium nitrite, or its equivalent to form the desired final product.

In general, the reaction temperatures are relatively low as indicated in the following Example, and reaction times are reasonable.

In the preparation of intermediate II, usually from about 1 to 3 moles of hydrazine are employed per mole of starting reactant, methyl-2-methoxy-4-acetylamino-5-nitrobenzoate, and most preferably, 2 moles of hydrazine are employed per mole of said methyl ester. The reaction temperature for the preparation of intermediates I and II is generally from about 80° to 105° C., preferably from about 85° C. to 95° C. and, most preferably, about 90° C.

In the preparation of intermediate III, normally from about 2 to 6 moles, preferably 5 moles, of acetic anhydride are employed per mole of intermediate II. The reaction temperature for this step is preferably maintained at from about 45° to 55° C. and, most preferably, at about 50° C.

In the preparation of intermediate IV, for most purposes from about 1 mole of lower alkyl chloroformate is employed per mole of intermediate III. The reaction temperature is preferably maintained at 0° C. In the preparation of intermediate V, preferably 1 mole of 2,5-dihalopentylamine is employed per mole of intermediate IV. The reaction temperature is maintained, generally, at room temperature for this step.

In the preparation of intermediate VI, usually 10 to 20 moles of allylamine are employed per mole of intermediate V. The reaction temperature is the temperature of reflux.

In the preparation of the desired final product from intermediate VI, from about 1 to 2 moles, preferably 1.5 moles, of sodium nitrite is employed per mole of intermediate VI and from about 2 to 5 moles of hydrochloric acid in methanol is employed per mole of intermediate VI.

Each of the steps of the process of the invention is preferably carried out at atmospheric pressure.

The following Example illustrates a preferred embodiment of the invention and is not limitative of scope.

EXAMPLE

Preparation of 2-methoxy-4,5-diaminobenzoic acid

Using a 4 litre balloon flask provided with an agitator, a thermometer, a condenser and a dropping funnel, 132.3 g (0.494 mole) of methyl 2-methoxy 4-acetylamino-5-nitrobenzoate, 1320 ml of water and 130 g of 40% soda lye were introduced. The mixture was heated for 4 hours under reflux (temperature in the mass: 100° C.), the temperature allowed to drop to about 90° C., 12.5 g of Raney nickel was added and 51.6 g (1.03 mole) of hydrazine hydrate added, dropwise, so as to maintain the reaction temperature at about 90° C. without the application of heat from the outside. The solution should be totally decolorized at the end of the addition, otherwise a little more hydrazine should be added to permit such decolorization.

The solution was then refluxed for a further hour and left to stand overnight. Vegetable carbon black was added; the solution was filtered; washed three times with 40 ml of water to remove carbon black and the filtrate acidified to a pH-value of 4.9 with 9.7 g (8.2 ml) of hydrochloric acid, (specific gravity=1.18).

The product was left to crystallise for three hours in a refrigerator, and drained, and the crystals were washed four times with 120 ml of water and dried overnight in a drying oven at 50° C.

Yield=79 to 82 g (88%–91%).
MP=198° C.

Preparation of 2-methoxy-4,5-diacetylaminobenzoic acid

Using a 2 liter balloon flask provided with an agitator, a thermometer, a condenser and a dropping funnel, 142 g (0.78 mole) of 2-methoxy-4,5-diaminobenzoic acid and 710 ml of water were introduced. The resulting suspension was heated to a temperature of 45° to 50° C. and 442 g (4.33 moles) of acetic anhydride was added dropwise. The suspension decolorized and thickened. The suspension was then agitated for 1.5 hours at a temperature of 50°±1° C., and left to stand overnight. The resulting solid was drained, washed with water and dried in a drying oven at 50° C.

Yield=174–178 g (84%–86%).
MP is greater than 260° C. (Kofler).

The NMR spectrum was compatible with the structure of the expected product.

Preparation of N- (2',5'-dichloropentyl) 2-methoxy-4,5-diacetylaminobenzamide

Using a 500 ml balloon flask provided with an agitator, a thermometer, a condenser and a dropping funnel, 26.6 g (0.1 mole) of 2-methoxy-4,5-diacetylaminobenzoic acid, 260 ml of acetone, 13.9 ml of triethylamine and 60 ml (56.7 g) of dimethylformamide were admixed. The mixture was agitated at room temperature for 2.5 hours (until total dissolution of the acid occurs), and cooled to 0° C. Thereafter 10.85 g (9.5 ml), (or 0.1 mole) of ethylchloroformate was added dropwise. The mixture was reacted for 45 minutes at 0° C., followed by the addition of 21.3 g (0.110 mole) of 2,5-dichloropentylamine hydrochloride in small portions for a period of 5 minutes. Then, 15.3 ml to triethylamine (in all, 29.2 ml or 21.2 g=0.210 mole) was added dropwise.

The system was allowed to return to room temperature, and then agitated for 3 hours. The resulting suspension was poured into 550 ml of water. Solubilization occurred, immediately followed by the appearance of a precipitate. The precipitate was left to crystallise overnight in a refrigerator. Thereafter, the precipitate was removed, washed five times with 60 ml of water and dried in a drying oven at a temperature of 50° C.

Yield=33 g (82%).
MP=154.157° C.

The NMR spectrum was compatible with the structure of the expected product.

Cl %-found=17.48-calculated=17.57.

Preparation of N-[(1'-allyl-2'-pyrrolidinyl) methyl]-2-methoxy-4,5-diacetylaminobenzamide Using a 250 ml balloon flask provided with an agitator, a thermometer and a condenser, 16.2 g (0.04 mole) of N-(2',5'-dichloropentyl) 2-methoxy-4,5-diacetylaminobenzamide and 46 g (60 ml=0.8 mole) of allylamine were admixed to form a suspension.

The suspension was agitated at 20° C. and refluxed for three hours. The excess allylamine was evaporated and the residual oil was dissolved in 100 ml of water at 40° C. A product crystallized. Thereafter, 8 ml of 40% soda lye was added and the system was permitted to crystallise for 3 hours at 20° C. The crystals were drained, washed with water and the resulting solid was dried in a drying oven at 50° C.

Yield=11.2 g (72%).

The product was recrystallized from a mixture of 200 ml of ethylacetate and 20 ml of ethanol, at boiling temperature. (MP=155° C).

The NMR spectrum was compatible with the structure of the expected product.

Preparation of N-[(1'-allyl-2'-pyrrolidinyl) methyl]-2-methoxy-4,5-azimidobenzamide Using a 500 ml balloon flask provided with an agitator, a thermometer and a dropping funnel, 112 ml of methanol and 3.10 g (0.045 mole) of sodium nitrite were admixed. The system was agitated to dissolve the components and then a solution of 11.6 g (0.03 mole) of N-[(1'-allyl 2'-pyrrolidinyl) methyl]-2-methoxy-4,5-diacetylamino benzamide in 75 ml of methanol was added.

To this reaction mix was added, slowly, 63.6 ml (0.135 mole) of 2.12 N hydrochloric methanol with cooling in order to maintain the temperature at 20° C. The solution, which was clear at the beginning, became cloudy and, after standing for 48 hours at room temperature, the solvent was evaporated under vacuum. The resulting oily residue was dissolved hot in 50 ml of isopropanol. Then, 2.7 g of insoluble sodium chloride was filtered off and the filtrate was permitted to crystallize for 2 hours in a refrigerator.

The product was drained, washed with 5 ml of iced isopropanol, and then dried in a drying oven at 50° C.

Yield=8.6 g (79%).

Kofler MP=202°-203° C.

The NMR spectrum was similar to that of a reference sample.

The invention is not to be limited except as set forth in the following claims:

What is claimed is:

1. Process for preparing N-[(1'-allyl-2'-pyrrolidinyl)-methyl]-2-methoxy-4,5-azimidobenzamide comprising, in sequence:
   (a) reacting methyl-2-methoxy-4-acetylamino 5-nitrobenzoate with sodium hydroxide and then reducing the resulting sodium 2-methoxy-4-amino-5-nitrobenzoate intermediate with hydrazine in the presence of Raney nickel at ambient pressure to form a 2-methoxy-4,5-diaminobenzoic acid intermediate;
   (b) reacting the 2-methoxy-4,5-diaminobenzoic acid intermediate with acetic anhydride to form a 2-methoxy-4,5-diacetylaminobenzoic acid intermediate;
   (c) reacting the 2-methoxy-4,5-diacetylaminobenzoic acid intermediate with a lower alkyl chloroformate to form a mixed lower alkanoic-benzoic anhydride intermediate of said 2-methoxy-4,5-diacetylaminobenzoic acid intermediate which is then treated with a dihalopentyl amine at ambient temperature to form a N-(2',5'-dihalopentyl)-2-methoxy-4,5-diacetylaminobenzamide intermediate;
   (d) reacting the N-(2',5'-dihalopentyl)-2-methoxy-4,5-diacetylaminobenzamide intermediate with allylamine to form a N-[(1'-allyl-2'-pyrrolidinyl)methyl]2-methoxy-4,5-diacetylaminobezamide intermediate; and
   (e) reacting the N-[(1'-allyl-2'-pyrrolidinyl)methyl]-2-methoxy-4,5-diacetylaminobenzamide intermediate with sodium nitride at ambient temperature.

* * * * *

UNITED STATES PATENT AND TRADEMARK OFFICE
CERTIFICATE OF CORRECTION

PATENT NO. : 4,804,765

DATED : February 14, 1989

INVENTOR(S) : JACQUES ACHER, ET AL.

Page 1 of 3

It is certified that error appears in the above-identified patent and that said Letters Patent is hereby corrected as shown below:

IN [54] TITLE

"2'PYRROLIDINYL)" should read --2'-PYRROLIDINYL)--.
"METHYL]2" should read --METHYL]-2--.

IN [73] ASSIGNEE

"Societe D'Etudes Scientifiques et Industrielles de L'Ile-d-France, Paris, France" should read --Societe D'Etudes Scientifiques et Industrielles de L'Ile-de-France, Paris, France--.

IN [30] FOREIGN APPLICATION PRIORITY DATA

"France ...... 84 19322" should read --France ...... 84-19322--.

COLUMN 1

Line 3, "2'PYRROLIDINYL)" should read --2'-PYRROLIDINYL)--.
Line 4, "METHYL]2" should read --METHYL]-2--.
Line 9, "methyl]2" should read --methyl]-2--.
Line 38, "amine" should read --amine.--.
Line 41, "2-methoxy 4,5-" should read --2-methoxy-4,5- --.
Line 43, "N-allyl 2-" should read --N-allyl-2- --.

UNITED STATES PATENT AND TRADEMARK OFFICE
CERTIFICATE OF CORRECTION

PATENT NO. : 4,804,765
DATED : February 14, 1989
INVENTOR(S) : JACQUES ACHER, ET AL.　　　　Page 2 of 3

It is certified that error appears in the above-identified patent and that said Letters Patent is hereby corrected as shown below:

COLUMN 2

Line 13, "diacetylminobenza-" should read --diacetylaminobenza--.
    Line 26, "to" should be deleted.
    Line 31, "DETAIL" should read --DETAILED--.

COLUMN 4

Line 40, "to" should read --of--.

COLUMN 5

Line 17, "N-[(1'-allyl 2'-pyrrolidinyl)" should read --N-[(1'-allyl-2'-pyrrolidinyl)--.

UNITED STATES PATENT AND TRADEMARK OFFICE
CERTIFICATE OF CORRECTION

PATENT NO. : 4,804,765
DATED : February 14, 1989
INVENTOR(S) : JACQUES ACHER, ET AL.   Page 3 of 3

It is certified that error appears in the above-identified patent and that said Letters Patent is hereby corrected as shown below:

COLUMN 6

Line 2, "claims:" should read --claims.--.
    Line 7, "acetylamino 5-" should read --acetylamino-5- --.
    Line 30, "thyl]2" should read --thyl]-2--.
    Line 34, "sodium nitride" should read --sodium nitrite--.

Signed and Sealed this

Twelfth Day of December, 1989

Attest:

JEFFREY M. SAMUELS

*Attesting Officer*    Acting Commissioner of Patents and Trademarks